United States Patent
Raupach et al.

(10) Patent No.: US 11,039,786 B2
(45) Date of Patent: Jun. 22, 2021

(54) METHOD AND APPARATUS FOR DETERMINING A PATIENT WEIGHT AND/OR A BODY MASS INDEX

(71) Applicant: Siemens Healthcare GmbH, Erlangen (DE)

(72) Inventors: Rainer Raupach, Heroldsbach (DE); Andreas Krauss, Bubenreuth (DE); Andreas Wimmer, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 135 days.

(21) Appl. No.: 16/412,711

(22) Filed: May 15, 2019

(65) Prior Publication Data
US 2019/0357844 A1 Nov. 28, 2019

(30) Foreign Application Priority Data

May 23, 2018 (EP) .................................... 18173815
Dec. 14, 2018 (EP) .................................... 18212734

(51) Int. Cl.
*G06K 9/00* (2006.01)
*A61B 5/00* (2006.01)
*G06T 7/593* (2017.01)
*A61B 6/03* (2006.01)
*G06T 11/00* (2006.01)

(52) U.S. Cl.
CPC .......... *A61B 5/4872* (2013.01); *A61B 5/0077* (2013.01); *A61B 6/032* (2013.01);
(Continued)

(58) Field of Classification Search
CPC ....... A61B 6/032; A61B 6/544; A61B 5/0077; A61B 5/4872; A61B 5/7264; A61B 5/0064; A61B 6/5258; G06T 11/005; G06T 2207/10028; G06T 2207/20081; G06T 2207/10081; G06T 2207/30004;
(Continued)

(56) References Cited

U.S. PATENT DOCUMENTS

2006/0067461 A1  3/2006  Yin et al.
2014/0270053 A1  9/2014  Larson
(Continued)

FOREIGN PATENT DOCUMENTS

DE   10 2016 209 674 A1   12/2017

OTHER PUBLICATIONS

Touch, Mengheng, et al. "A neural network-based method for spectral distortion correction in photon counting x-ray CT." Physics in Medicine & Biology 61.16 (2016): 6132. (Year: 2016).*
(Continued)

*Primary Examiner* — Li Liu
(74) *Attorney, Agent, or Firm* — Harness, Dickey & Pierce, P.L.C.

(57) ABSTRACT

A method is for determining a patient weight and/or a body mass index of a patient. The method includes acquiring image data containing depth information of the patient; generating a surface model of the patient based upon the image data acquired; determining density information or X-ray attenuation information of at least part of the patient; and determining at least one of the total patient weight and the body mass index of the patient using the surface model generated and the density information or X-ray attenuation information determined.

23 Claims, 4 Drawing Sheets

(52) U.S. Cl.
CPC ............ *G06T 7/593* (2017.01); *G06T 11/005* (2013.01); *G06T 2207/10028* (2013.01); *G06T 2207/10081* (2013.01); *G06T 2207/20081* (2013.01); *G06T 2207/30004* (2013.01); *G06T 2211/40* (2013.01)

(58) Field of Classification Search
CPC ....... G06T 2211/40; G06T 2207/10116; G06T 2207/20084
See application file for complete search history.

(56) References Cited

U.S. PATENT DOCUMENTS

| | | | |
|---|---|---|---|
| 2016/0262713 A1 | 9/2016 | Flohr | |
| 2016/0262714 A1 | 9/2016 | Krauss et al. | |
| 2017/0249423 A1 | 8/2017 | Wang et al. | |
| 2017/0352166 A1 | 12/2017 | Raupach | |
| 2018/0182096 A1* | 6/2018 | Grady | G16H 50/50 |
| 2019/0057521 A1* | 2/2019 | Teixeira | A61B 6/5205 |

OTHER PUBLICATIONS

Williamson, Jeffrey F. et al. "On two-parameter models of photon cross sections: Application to dual-energy CT imaging", Medical Physics, vol. 33, No. 11; Nov. 2006, pp. 4115-4129, DOI:10.1118/1.2349688; 2006.
Alvarez, R. et al.: "Energyselective Reconstructions in X-Ray Computerized Tomography", in: Phys. Med. Biol., 1976, vol. 21, No. 5, pp. 733-744, doi: 10.1088/0031-9155/21/5/002.
Extended European Search Report dated Jul. 24, 2019.

* cited by examiner

METHOD AND APPARATUS FOR DETERMINING A PATIENT WEIGHT AND/OR A BODY MASS INDEX

PRIORITY STATEMENT

The present application hereby claims priority under 35 U.S.C. § 119 to European patent application numbers EP 18173815.4 filed May 23, 2018, and EP 18212734.0 filed Dec. 14, 2018, the entire contents of each of which are hereby incorporated herein by reference.

FIELD

Embodiments of the invention generally relate to a method and an apparatus for determining a patient weight and/or a body mass index, and to a computer program product comprising a computer program and a computer-readable medium on which program sections that can be read in and executed by a processing unit are stored for carrying out the method according to an embodiment of the invention.

BACKGROUND

Knowledge of the patient weight is required for particular purposes, e.g. patient-specific administration of CT contrast agent. The object of the invention is to determine the patient weight and/or a body mass index without having to measure the patient weight directly using a mechanical weighing scale.

SUMMARY

The conventional way of measuring weight is by way of a weighing scale on which the patient is physically positioned. However, the inventors have discovered that this constitutes an additional step in the workflow and therefore takes up additional time.

The inventors note that the weighing scale could also be directly incorporated in the CT table to avoid an additional work step. However, they have discovered that this leads to increased hardware costs.

There are also approaches whereby the weight is deduced from the weight-dependent inertia of the table during horizontal acceleration, e.g. by measuring the motor current necessary for a particular acceleration.

The inventors have discovered that one solution would be to estimate the patient weight via the volume and using an assumed average density, from a surface model of the body determined using an optical 3D camera. However, the inventors have discovered that the problem with exclusively surface-based weight estimation is that significantly different weights may be obtained for the same patient volume, e.g. because of a different body fat percentage.

Embodiments of the invention are directed to, for example, a method which can determine a weight and/or a body mass index of a patient with low cost/complexity but with a high degree of accuracy.

At least one embodiment is directed to a method for determining a patient weight and/or a body mass index of a patient, comprising:
  acquiring image data containing depth information of the patient,
  generating a surface model of the patient on the basis of the image data,
  determining (mass) density information or X-ray attenuation information of at least part of the patient, and
  determining a total patient weight and/or the body mass index of the patient using the surface model and the, in particular partial, density information or X-ray attenuation information.

In addition to at least one embodiment of the inventive method, at least one embodiment of the invention also relates to an apparatus for determining a patient weight, having
  an interface for acquiring image data containing depth information of the patient;
  a generating unit for generating a surface model of the patient based on the image data;
  an interface for acquiring (mass) density information or X-ray attenuation information of at least part of the patient,
  a calculating unit for determining a total patient weight and/or the body mass index of the patient using the surface model and the mass density information or X-ray attenuation information of at least part of the patient, and
  an output unit for outputting the determined patient weight and/or the body mass index of the patient.

Further, at least one embodiment of the invention also relates to an apparatus for determining at least one of a total patient weight and a body mass index of a patient, comprising:
  at least one interface to acquire image data containing depth information of the patient and to acquire density information or X-ray attenuation information of at least part of the patient;
  at least one processor to generate a surface model of the patient based on the image data acquired and determine at least one of the total patient weight and the body mass index of the patient using the surface model generated and the density information or X-ray attenuation information of at least part of the patient acquired; and
  an output device to output the at least one of the total patient weight and the body mass index of the patient determined.

At least one embodiment of the invention further relates to a computer program product comprising a computer program which can be loaded directly into a storage device of a control device or of a computing apparatus, having program steps for carrying out all the steps of the method of at least one embodiment of the invention when the computer program is executed in the control device or the computing apparatus. As already explained, in respect of acquiring the image data or determining the (mass) density information or X-ray attenuation information it is in principle sufficient if this information is provided by an external device or another computer program. However, the computer program can also have program sections which determine the (mass) density information, e.g. as explained above, from X-ray data and/or which control an image acquisition device(s) for acquiring the image data and/or an X-ray device for determining corresponding X-ray data or the X-ray attenuation information.

At least one embodiment of the invention also relates to a computer-readable medium on which are stored program steps that can be read in and executed by a processing unit in order to carry out all the steps of the method of at least one embodiment of the invention when the program sections are executed by the processing unit. The program sections can in particular constitute the above mentioned computer program. The processing unit can constitute the control device or computing apparatus or a part thereof.

At least one embodiment of the invention also relates to a method for training an algorithm for determining a total patient weight and/or a body mass index of a patient using a surface model of the patient and (mass) density information or X-ray attenuation information of at least part of the patient. The algorithm can be trained by supervised learning on the basis of a plurality of training data sets. In particular, a neural network can be trained as the algorithm. Details relating to training the algorithm and providing the training data sets have already been explained in the foregoing.

At least one embodiment of the invention also relates to an algorithm trained by the method described for determining the total patient weight and/or the body mass index of a patient, and to a data medium which stores the algorithm or parameters that have been determined as part of the training.

At least one embodiment of the invention also relates to a non-transitory computer program product comprising a computer program, directly loadable into a storage device of at least one of a control device and a computing apparatus, including program sections for carrying out at least one embodiment of the method upon the program sections of the computer program being executed in the at least one of the control device and the computing apparatus.

At least one embodiment of the invention also relates to a non-transitory computer-readable medium, storing a computer program including program sections, readable and executing by at least one processor, to carry out at least one embodiment of the method upon the program sections of the computer program being executed by the at least one processor.

BRIEF DESCRIPTION OF THE DRAWINGS

Further advantages and details of the invention will emerge from the following example embodiments and the associated schematic drawings in which.

DETAILED DESCRIPTION OF EXAMPLE EMBODIMENTS

Figure 1:
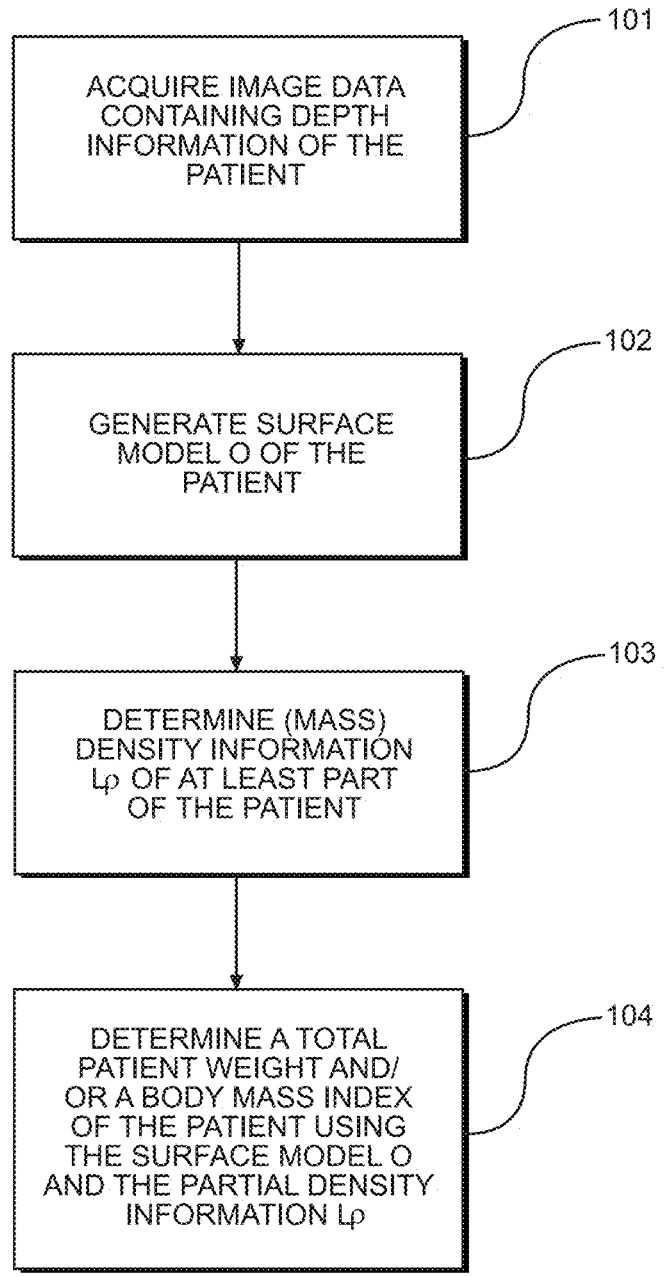
FIG. 1 illustrates an example embodiment of the method according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to a method for determining a patient weight and/or a body mass index of a patient, comprising:
  acquiring image data containing depth information of the patient,
  generating a surface model of the patient on the basis of the image data,
  determining (mass) density information or X-ray attenuation information of at least part of the patient, and
  determining a total patient weight and/or the body mass index of the patient using the surface model and the, in particular partial, density information or X-ray attenuation information.

It is therefore proposed in at least one embodiment, as part of calculating a patient weight or a body mass index, to take into account not only a surface model of the patient from which in particular a patient volume is known, but also information about the density or mass density of at least part of the patient or the X-ray attenuation in at least part of the patient. The terms patient weight and total patient weight and the terms density information, mass density information and (mass) density information are used interchangeably here.

Taking additional information about the density of the patient into account enables the accuracy of the determined patient weight and/or body mass index to be significantly improved compared to merely taking the patient volume into account, as effects of different body fat percentages, for example, can be allowed for at least approximately. The density information can only describe an average density of the patient or of part of the patient. However, the density information preferably has spatial resolution. The density information can basically be three-dimensional, i.e. contains information in respect of the density for individual volume portions or voxels. However, as will be explained more precisely below, spatially resolved density information can be acquired particularly simply if line integrals of the density are determined along a plurality of rays through the patient's body. Since, as explained, density information in respect of the entire volume of the patient is not necessarily available for determining the total patient weight and/or body mass index of the patient, partial density information, i.e. particularly density information relating to only a sub-volume of the patient, is typically taken into account as part of the determination. However, it is self-evidently also possible to take density information in respect of the entire volume of the patient into account if such information is available.

As will be explained in greater detail below, in at least one embodiment X-ray attenuation information, which can be determined e.g. from X-ray projection data or from a CT reconstruction on the basis of a plurality of X-ray projections, can be a measure for the mass density in the patient and therefore also considered as a special case of (mass) density information. In a narrower interpretation of the term (mass) density information, it could also be postulated that this explicitly describes a mass density or more specifically e.g. a line integral of the mass density. Such (mass) density information can be calculated from X-ray attenuation information, as will be described in greater detail below.

Acquiring image data is to be understood here as meaning, on the one hand, that the image data is determined on the basis of a corresponding sensor system. On the other hand, however, acquiring image data can also be understood as meaning that it is provided by an external device and acquired by a server or other processing device via a communication link. Likewise, determining the density information or X-ray attenuation information can include sensor-based acquisition of input data from which this information is determined. However, it is also possible for the density information to be determined from separately provided input data which can be provided e.g. by a third-party device via a communication link.

The image data with depth information can be in particular 3D image data.

The image data with depth information may have been acquired in particular by a 3D image camera. In particular, the image data can be acquired or may have been acquired using an optical 3D camera. As explained in the introduction, the method according to the invention can be relevant in particular in the context of computed tomography or for taking a patient weight and/or body mass index into account in other medical examination modalities. For these it is frequently necessary in any case to ensure correct patient positioning and/or take it into account for planning scan data acquisition. Corresponding 3D cameras are often present anyway in newer computed tomography systems or in other medical examination devices.

The surface model can be a patient model, also termed an avatar, or provided as a part thereof. As the image data includes depth information, it maps the surface of the patient directly, so that in the simplest case a surface model can be created by segmentation of the patient in the image data. Particularly advantageously, however, the surface model can be extracted from the image data using a machine learning based method. The principle of extracting a surface model from image data with depth information using machine learning based methods is well known in the prior art and will not therefore be explained in greater detail.

The (mass) density information can be obtained in particular from an X-ray measurement of the patient. In particular, the (mass) density information can be determined from X-ray projection data, in particular from X-ray projection data of a topogram image, or from reconstructed image data of a native CT scan.

Correspondingly, the X-ray attenuation information can be determined from an X-ray measurement of the patient. In particular, the X-ray attenuation information can be X-ray projection data, in particular X-ray projection data of a topogram image, or reconstructed image data of a native CT scan. The (mass) density information can be determined from the X-ray attenuation information.

In at least one embodiment, the X-ray projection data can be generated in particular when taking a topogram, as is carried out to prepare tomographic examinations on a computed tomography device (CT device). Here one or more separate projections, i.e. two-dimensional images, are taken which are used for examination planning. For example, a topogram is used to precisely define the actual scanning area for a CT examination, i.e. in particular for three-dimensional data acquisition. As corresponding X-ray projection data is therefore acquired anyway during a regular CT examination procedure, no additional radiation needs to be applied for the purpose of weight determination using this data. The (mass) density information or X-ray attenuation information can therefore be determined on the basis of input data which is available anyway and is only used for an additional function as part of the method described. The method according to at least one embodiment of the invention can therefore be deployed particularly simply, without additional radiation load for the patient and essentially without additional time requirement.

When using the method according to at least one embodiment of the invention, in some applications a reconstructed image data set, in particular a reconstructed image data set of a native CT scan, i.e. a scan without contrast agent, may already be available which can then be used to determine the density information or can be used as X-ray attenuation information. For example, at least one embodiment of the inventive determination of the patient weight and/or body mass index can be used to determine how much contrast agent needs to be used.

In contrast-agent-using computed tomography methods, mask images or corresponding reconstructed mask image data sets which were obtained without prior contrast agent administration are frequently used. Already reconstructed image data of a native CT scan may therefore be available when the patient weight and/or body mass index is to be determined for parameterization of contrast agent administration. A spatial attenuation distribution is therefore available from which the density distribution can be determined.

In the simplest case, attenuation values can be mapped to mass density values. This is known in principle from radiation therapy planning.

Alternatively, mass density distributions can be reconstructed indirectly using multimaterial decompositions. This is known e.g. from the publication DE 10 2016 09674 A1, the entire contents of which are hereby incorporated herein by reference. If multienergy topograms or multienergy CT images are used which can be obtained in particular using photon-counting detectors, methods are also known for calculating mass density line integrals or spatial mass density distributions on the basis of material decompositions, e.g. from the following articles: R. E. Alvarez and A. Macovski, "Energy-selective reconstructions in X-ray computerized tomography," Phys. Med. Biol., 21 (5), pp. 733-744, 1976, Williamson et. al., "On two-parameter models of photon cross sections: Application to dual-energy CT imaging," Med. Phys. 33 (11), pp. 4115-4129, 2006, the entire contents of each of which are hereby incorporated herein by reference.

The X-ray projection data is preferably corrected by beam hardening correction, wherein the (mass) density information is determined from the X-ray projection data corrected in this way. Alternatively, beam hardening correction can also be used to determine X-ray attenuation information from the X-ray projection data, which information is then used to calculate the total patient weight and/or body mass index. X-ray projection data typically defines signal attenuation in the individual pixels for a known applied X-ray spectrum. However, as the local absorption and scattering depend on the frequency and energy respectively of the incident radiation, the following line integral initially results for the measured line integrals $L\mu$ of the attenuation:

$$L_\mu = -\ln(I/I_0) = -\ln(\int I(E)\exp(-\int \mu(E,\vec{r})d\vec{r})dE/\int I(E)dE)$$

where $I_0$ is the incident intensity of the X-radiation and I the detected intensity of the X-radiation. I(E) is the energy-dependent intensity distribution of the incident X-radiation and $\mu(E,r)$ is the energy-dependent absorption coefficient at the position r.

It is known that, on penetrating matter, the X-radiation spectrum is shifted toward higher energies as the penetration depth increases because the higher-energy photons are less scattered. In an imaging context, this effect potentially results in scanning artifacts in the case of non-energy-resolved detection of the X-radiation intensity. It has been recognized that the density information may also be corrupted by this effect if it is calculated directly from the X-ray projection data.

It is therefore proposed to determine the density information on the basis of corrected X-ray projection data obtained by applying a beam hardening correction to the X-ray projection data. The corrected X-ray projection data $L_\mu'$ is here determined as a function f(x) of the X-ray projection data $L_\mu$:

$$L_\mu' = f(L_\mu),$$

where the function f(x) is preferably a polynomial, i.e. can be written in the $$f(x) = \sum_k a_k x^k.$$

The coefficents $a_k$ can be determined by carrying out reference scans on objects having a known distribution of an energy-independent absorption coefficient for a particular incident X-ray spectrum, particularly phantom scans. Alternatively or in addition, X-ray imaging simulations can be used. The coefficients $a_k$ are then selected such that the following condition is fulfilled:

$$L_\mu' \approx \int \mu'(\vec{r})d\vec{r}$$

Here the energy-independent absorption coefficients $\mu'$ can be calculated, for example, by weighting the energy-dependent absorption coefficients on the basis of the known spectrum of the incident X-radiation. In terms of the reference scan, in particular water can be used for the absorption, as it can be assumed that all the materials present in the body are in leading order watery.

From the X-ray projection data or the corrected X-ray projection data, an integrated density can be calculated for each pixel of the X-ray projection data as (mass) density information on the assumption of the same irradiated material, wherein, in particular, irradiation of water is assumed. The attenuations of different strengths are therefore considered, to an approximation, as pure density differences, i.e.

$$L_\mu' \approx \int \mu'(\vec{r})d\vec{r} \approx \mu_{H_2O} \int \rho(\vec{r})/\rho_{H_2O}(\vec{r})d\vec{r} = \mu_{H_2O}/\rho_{H_2O}(\vec{r}) \underbrace{\int \rho(\vec{r})d\vec{r}}_{=L_\rho}.$$

where $\mu_{H_2O}$ is the attenuation coefficient of water and $\rho_{H_2O}$ the density of water. The X-ray projection data $L_\mu$ or the corrected X-ray projection data $L_\mu'$ are therefore proportional with a known proportionality factor to an integral along the respective X-ray over the density $\rho(r)$ of the irradiated patient at the respective position r. These density integrals $L_\rho$ can therefore be specified as (mass) density information:

$$L_\rho \approx L_\mu' \cdot \rho_{H_2O}/\mu_{H_2O} = \rho_{H_2O}/\mu_{H_2O} \cdot f(L_\mu).$$

As the (mass) density information is approximately proportional with a known proportionality factor to the X-ray projection data, i.e. to X-ray attenuation information, the X-ray attenuation information itself can also be regarded as (mass) density information. Alternatively, as explained above, the (mass) density information can be determined from the X-ray attenuation information in an intermediate step in order to then use the (mass) density information to determine the total patient weight and/or body mass index.

In at least one embodiment of the invention, the determining step can take place using a machine learning method, in particular using a trained algorithm. In particular, a trained neural network or rather an algorithm appropriately trained in a neural network can be used here.

The patient's total weight and/or body mass index is preferably determined with the aid of a machine learning based approach using the surface model and the (mass) density information or X-ray attenuation information as input data. The machine learning based approach can correspond to the above mentioned machine learning method. For example, a neural network, in particular a convolutional neural network, can be trained to determine the total patient weight and/or the body mass index from the surface model and the density information or X-ray attenuation information as input data.

Algorithms, e.g. neural networks which are trained in the context of machine learning, have a large number of parameters which are suitably selected for subsequent use as part of a learning process. In a neural network, these parameters can be, for example, the input weights of the individual neurons. An algorithm used in the method according to at least one embodiment of the invention for determining the total patient weight and/or body mass index can be trained in particular as part of supervised learning. Here a plurality of training data sets are provided which, in addition to the respective input data, i.e. the surface model and the density information or X-ray attenuation information, include the desired output data for this input data, i.e. the respective total patient weight and/or the respective body mass index.

For example, the desired output data for the training data sets can be determined in other ways for the corresponding patient on which this training data set was determined. For example, the patient can be weighed by a weighing scale in order to determine the total patient weight and/or a height can be additionally measured in order to determine the body mass index from the patient's height and weight. However, any other approaches for determining the total patient weight and/or body mass index can also be used to provide output data for the training data sets.

As part of the training of the algorithm, the latter can initially be parameterized randomly or in some other manner. The provisionally parametrized algorithm is applied to the input data of at least parts of the training data sets and the resulting outputs of the algorithm are compared with the setpoint values stored in the corresponding training data set in order to detect the extent to which the algorithm's parameterization must be changed. For example, for training a neural network, the well-known back propagation of error approach can be used.

In addition to at least one embodiment of the inventive method, at least one embodiment of the invention also relates to an apparatus for determining a patient weight, having

- an interface for acquiring image data containing depth information of the patient;
- a generating unit for generating a surface model of the patient based on the image data;
- an interface for acquiring (mass) density information or X-ray attenuation information of at least part of the patient,
- a calculating unit for determining a total patient weight and/or the body mass index of the patient using the surface model and the mass density information or X-ray attenuation information of at least part of the patient, and
- an output unit for outputting the determined patient weight and/or the body mass index of the patient.

The apparatus can be part of a medical imaging device, e.g. a CT scanner. The apparatus can alternatively be a control device, implemented separately from a medical imaging device, for controlling the imaging device, e.g. a scan setup computer. However, it is also possible for the apparatus to be used exclusively for evaluating the scan data.

For example, the apparatus can be a workstation computer which is used for evaluating scan data and cannot engage directly in the operation of a medical imaging device. It is also possible for the apparatus to be a server or to be implemented as a cloud of a plurality of computer devices which can, for example, receive, via a network, the image data and the (mass) density information or information from which the latter can be determined. The total patient weight and/or body mass index determined can then be further processed locally, provided for further use via this or another network or e.g. transmitted back to the medical imaging device for e.g. controlling contrast agent administration there or providing a user there with information relating to the control thereof. The output unit can be used for outputting to a user or to another component or device.

The apparatus can be further developed, as explained in the foregoing in connection with the method according to at least one embodiment of the invention. In particular, the calculating unit can incorporate a correction device(s) for carrying out the explained beam hardening correction and/or it can incorporate a density calculation device(s) for calculating the (mass) density information, as explained, from the X-ray projection data or the corrected X-ray projection data. The described units or device(s) of the apparatus can be implemented by a respective or common processor, in particular by corresponding program code/segments/modules, FPGA, ASIC or other components.

At least one embodiment of the invention further relates to a computer program product comprising a computer program which can be loaded directly into a storage device of a control device or of a computing apparatus, having program steps for carrying out all the steps of the method of at least one embodiment of the invention when the computer program is executed in the control device or the computing apparatus. As already explained, in respect of acquiring the image data or determining the (mass) density information or X-ray attenuation information it is in principle sufficient if this information is provided by an external device or another computer program. However, the computer program can also have program sections which determine the (mass) density information, e.g. as explained above, from X-ray data and/or which control an image acquisition device(s) for acquiring the image data and/or an X-ray device for determining corresponding X-ray data or the X-ray attenuation information.

At least one embodiment of the invention also relates to a computer-readable medium on which are stored program steps that can be read in and executed by a processing unit in order to carry out all the steps of the method of at least one embodiment of the invention when the program sections are executed by the processing unit. The program sections can in particular constitute the above mentioned computer program. The processing unit can constitute the control device or computing apparatus or a part thereof.

At least one embodiment of the invention also relates to a method for training an algorithm for determining a total patient weight and/or a body mass index of a patient using a surface model of the patient and (mass) density information or X-ray attenuation information of at least part of the patient. The algorithm can be trained by supervised learning on the basis of a plurality of training data sets. In particular, a neural network can be trained as the algorithm. Details relating to training the algorithm and providing the training data sets have already been explained in the foregoing.

At least one embodiment of the invention also relates to an algorithm trained by the method described for determining the total patient weight and/or the body mass index of a patient, and to a data medium which stores the algorithm or parameters that have been determined as part of the training.

FIG. 1 shows a flowchart of an example embodiment of a method for determining a total patient weight and/or a body mass index of a patient. In the example embodiments, to avoid unnecessary repetitions, the determination always takes place on the basis of (mass) density information which can be determined in particular according to X-ray data. Alternatively, it would also be possible to evaluate X-ray attenuation information directly, particularly if, as explained above, it can be assumed to be approximately proportional to corresponding (mass) density information.

This involves the following steps:

acquiring image data containing depth information of the patient (step 101);

generating surface model O of the patient (step 102);

determining (mass) density information Lρ of at least part of the patient (step 103); and determining a total patient weight and/or a body mass index of the patient using the surface model O and the partial density information Lρ (step 104).

Figure 3:
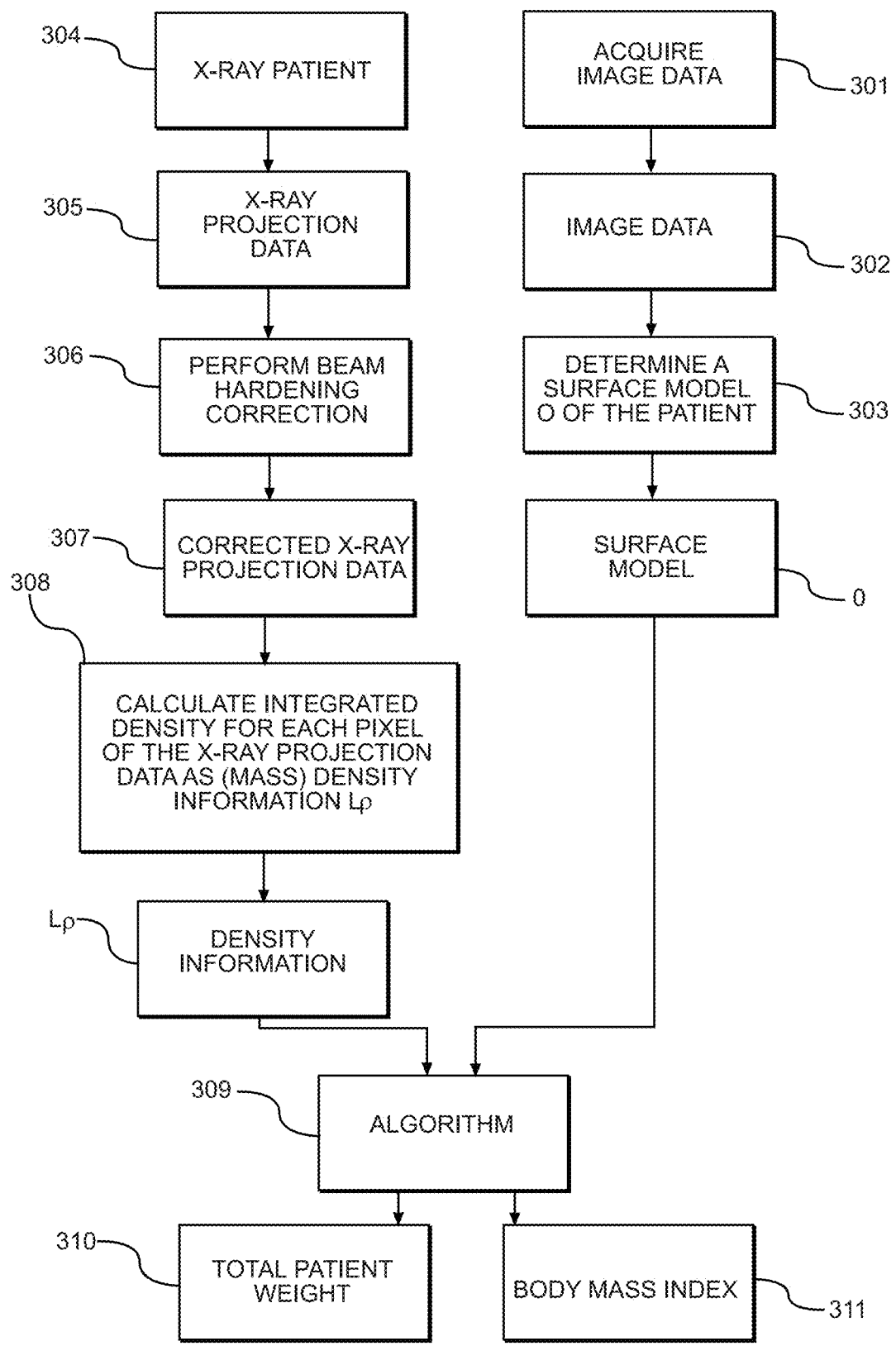
FIG. 3 shows the sequence of another example embodiment of the method according to the invention.

A possibility for organizing the individual steps 101 to 104 will be explained in greater detail later with reference to FIG. 3.

Figure 2:
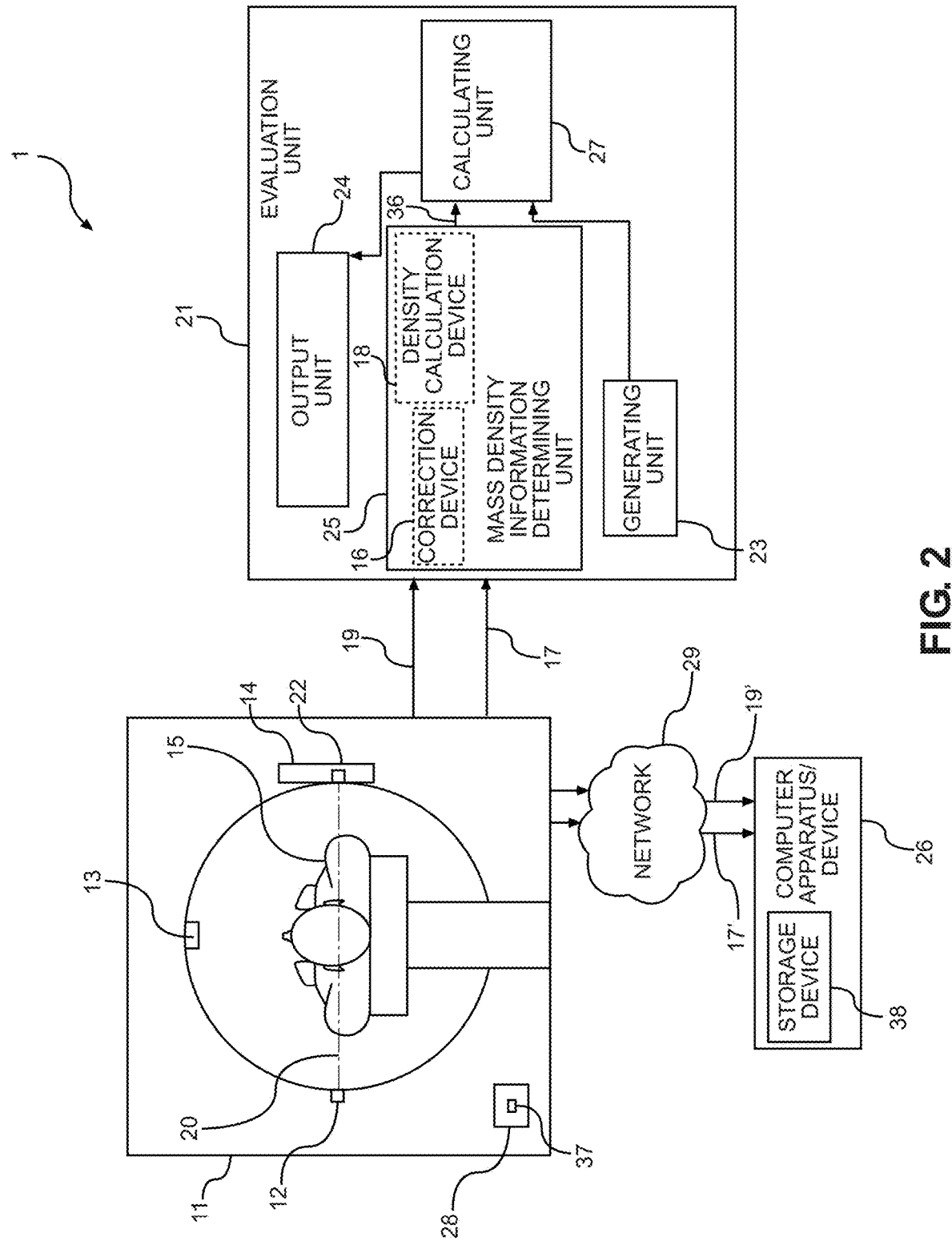
FIG. 2 illustrates an example embodiment of an apparatus according to the invention.

An example embodiment of the apparatus 1 of the invention is schematically illustrated in FIG. 2. In a CT device 11, image data containing depth information of a patient 15 can be acquired via a 3D camera 13. This image data is transmitted via an interface 17 to an evaluation unit 21 of the CT device 11. The surface model O of the patient is generated in a generating unit 23 for generating a surface model O of the patient.

In addition, (X-ray) projection measurement data can be acquired by the CT device 11 via a topogram image. Mass density information Lρ of at least part of the patient can be determined from the projection measurement data. The mass density information Lρ of at least part of the patient is transmitted via an interface 19 to the evaluation unit 21 of the CT device 11. In this case this information can be provided immediately to the calculating unit 27 via the interface 36. Alternatively, the projection measurement data can also be transmitted directly from the CT device and the calculation of the mass density information Lρ can take place in a mass density information determining unit 25 in the evaluation unit 21.

In the evaluation unit 21, the total patient weight and/or the body mass index can be calculated in a calculating unit 27 using the surface model O and the mass density information Lρ and output to an output unit 24. The output unit 27 can have a display, but can also be implemented merely as a data interface for outputting or transferring total patient weight data.

Further details of the apparatus 1 will be explained in the following with reference to FIG. 3 which shows a detailed example embodiment of a method for determining a total patient weight and a body mass index of the patient, as has already been discussed in more general terms with reference to FIG. 1. In step 301, image data is acquired using an optical 3D camera 13. For example, a stereo camera, a time-of-flight-method or similar can be used here. The resulting image data 302 therefore comprises not only brightness or color values for the individual pixels, i.e. two-dimensional image data, but also depth information for each individual pixel or groups of pixels.

Based on the image data 302, a surface model O of the patient 15 is determined in step 303. In the simplest case, this can be accomplished by segmenting the image region visualizing the patient 15, as the image data already describes the surface of the patient 15 because of the available depth information in this region. However, in the context of medical imaging, for generating a surface model O of the patient 15 it has generally been found to be particularly advantageous to use a method that has been trained as part of a machine learning process.

As will be explained in detail in the following, in parallel with the steps 301 and 303 or before, after or between these steps, (mass) density information Lρ is determined, as has already been described in general terms with reference to step 103 in FIG. 1. For this purpose the patient 15 is first X-rayed 304. For this purpose the X-ray source 12 is activated and the resulting X-radiation is measured by the X-ray detector 14 after passing through the patient 15. Individual detector elements 22 of the X-ray detector 14 measure the intensity of an X-ray 20 after it has passed through the patient 15. This produces X-ray projection data 305 in which the image data corresponds to the individual pixels, in each case from the line integral via the respective X-ray 20 which is assigned to the detector element 22 assigned to the pixel, via the attenuations along this ray 20. As will be explained in more detail below, information about the density of the patient 15 in the region of this ray 20 can be determined.

In principle, a plurality of X-ray projection images could also be acquired as part of the method, in particular in order to determine reconstructed image data of a CT scan. This would enable three-dimensional density information in respect of the patient 15 to be obtained. However, if such a three-dimensional 3D scan is not carried out anyway before the total patient weight and/or body mass index is to be determined, this would result in an unnecessarily high radiation load for the patient 15.

But as a topogram is typically taken anyway prior to CT examinations in order to precisely plan the examination, in particular the region of interest, the method according to an embodiment of the invention can be carried out using X-ray projection data without additional radiation load for the patient and without additional scanning time being required. However, in cases where reconstructed image data of a CT scan is determined anyway, e.g. if a mask data set is determined for CT angiography before contrast agent is administered, more precise information concerning the density distribution in the patient can be achieved by evaluating three-dimensional reconstructed image data and therefore the accuracy of a determined total patient weight and/or body mass index can potentially be increased still further.

In step 306, beam hardening correction is carried out for the X-ray projection data 305 in order to determine corrected X-ray projection data 307. As already explained above, this can be done by applying a function, in particular a polynomial, to the individual data points of the X-ray projection data.

In step 308, assuming that the same material is irradiated throughout the patient, wherein in particular irradiation of water is assumed, an integrated density is then calculated for each pixel of the X-ray projection data as (mass) density information Lρ. As already explained above, a proportionality factor can be determined on the basis of a known absorption coefficient for water for the X-radiation spectrum used and the density of water in order to determine this line integral of the density from the corrected X-ray projection data.

In order to put the described procedure into practice, the mass density information determining unit 25 can implement a correction device(s) 16 for carrying out the radiation hardening correction in step 306 and/or a density calculation device(s) 18 for determining the (mass) density information Lρ in step 308 from the corrected X-ray projection data 307.

The (mass) density information Lρ and the surface model O are fed to an algorithm 309 which, as will be explained in greater detail in the following, has been trained as part of a machine learning process to produce, as output data, the total patient weight 310 and a body mass index 311 of the patient 15. Alternatively it would self-evidently also be possible to determine only one of these values. The variables determined can be output, for example, on the output unit 24 of the evaluation unit 21. Alternatively or in addition, they can also be stored and/or used for subsequent evaluation in order to control other equipment, e.g. to control contrast agent administration to the patient 15.

In the previous examples it was assumed that the acquired image data 302 and X-ray projection data 305 is provided directly to an evaluation unit 21 which is implemented separately from the CT device 11 and carries out the entire further evaluation of the total patient weight 310 and/or body mass index 311. Alternatively, parts of this evaluation or even the entire determination can also be carried out by a control device 28 which can, for example, be incorporated in the CT device 11, as schematically illustrated in FIG. 2. This can be useful, for example, if contrast agent administration for the patient 15 is to be controlled directly or if data pre-processing already takes place anyway in the CT device 11. It would self-evidently also be possible to incorporate the evaluation unit 21 in the CT device 11 or use a separately implemented control device 28, e.g. a PC in a control room.

In some cases it may also be advantageous to carry out at least some of the above mentioned steps remotely from the CT device. For example, a computing apparatus 26 can be used which communicates with the CT device 11 via a network 29, e.g. the Internet. The interfaces 17', 19' of the computing apparatus 26 can in this case be network interfaces or can be addressed via a common network interface. The computing apparatus 26 can be implemented as an individual server, but can also be a cloud solution in which the functionality described can be provided jointly by a plurality of computing devices 26. In the control device 28 or computing apparatus 26 the described sequences can be implemented, for example, by loading a corresponding computer program into the respective storage device 37, 38 and executing it.

Figure 4:
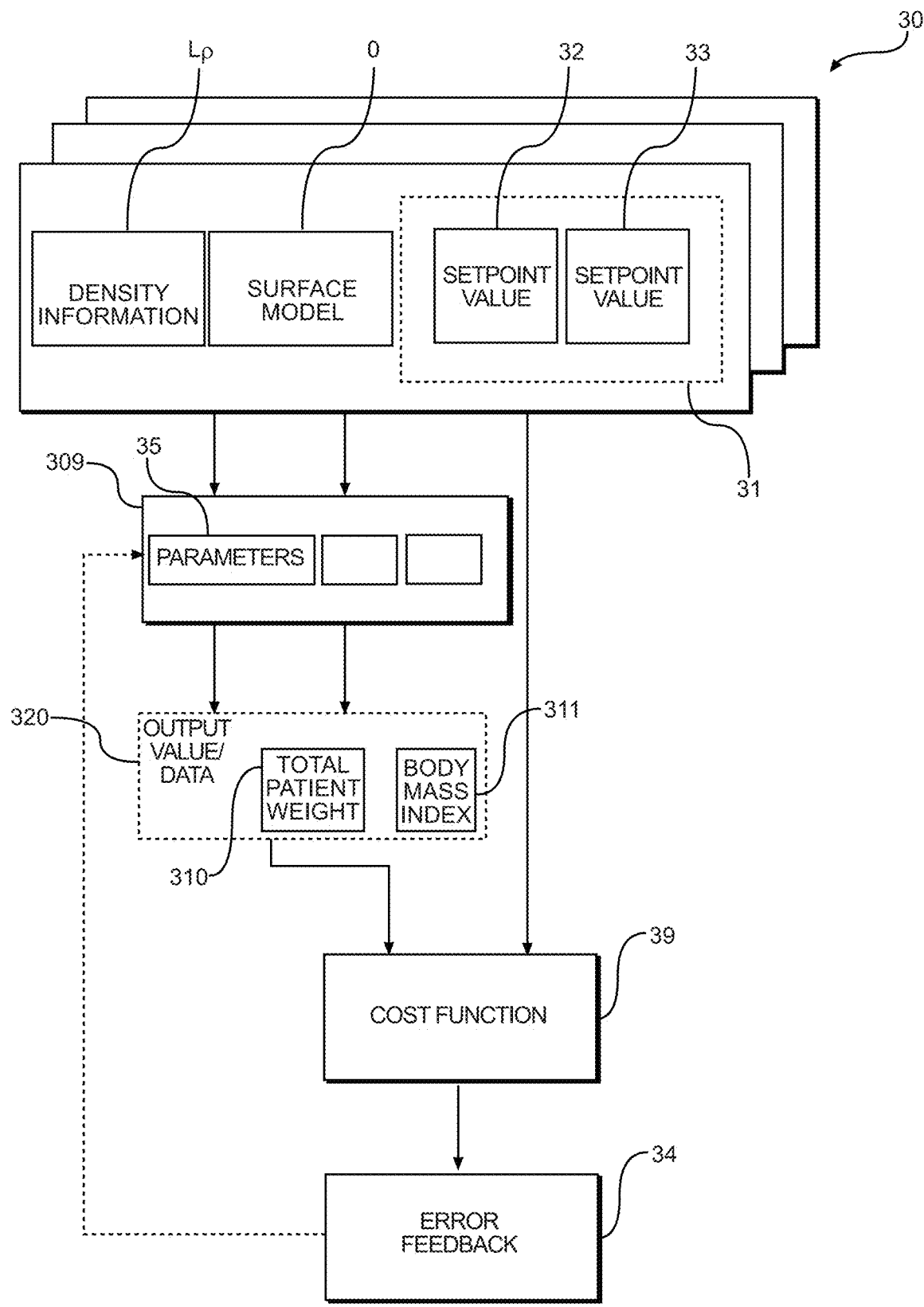
FIG. 4 shows an example embodiment for training an algorithm which can be used to determine a total patient weight and/or a body mass index of a patient from a surface model and density information or X-ray attenuation information.

FIG. 4 schematically illustrates a possibility for training the algorithm 309 as part of a machine learning process. The algorithm 309 has a plurality of parameters 35 whose values are defined by the learning process described below. The parameters 35 can be, for example, input weights of the artificial neurons of an artificial neural network.

In order to train the algorithm 309, i.e. select the parameters 35, a plurality of training data sets 30 are first provided. The training data sets 30 each comprise the (mass) density information $L\rho$ and the surface model O for a patient which can be determined as explained above. Each of the training data sets 30 additionally includes setpoint values 31 for the total patient weight 310 and the body mass index 311. These setpoint values 31 are variables which must be determined for the respective training data set 30 in an optimally trained algorithm 309. The setpoint value 32 for the total patient weight 310 can be determined, for example, by weighing the patient. If the weight of the patient is therefore known, the setpoint value 33 for the body mass index can be calculated in the normal way by dividing this weight by the square of the separately measured height of the patient 15.

The parameters 35 of the algorithm 309 are first initialized randomly or in some other way. Then, for some of the training data sets 30 the (mass) density information $L\rho$ and the surface model O are fed into the algorithm 309 as input data in order to determine output data 320 for the total patient weight 310 and the body mass index 311 for the respective training data set.

A cost function 39 is then evaluated, the value of which depends on the deviation of the output values 320 from the setpoint values 31. Depending on the cost function 39, error feedback 34 takes place in order to adjust the parameters 35 and therefore minimize the cost function 39 by repeating the described procedure a number of times.

A faster convergence can be achieved, for example, if the algorithm 309 can be differentiated. In this case, as part of error feedback 34 the derivative of the cost function can be evaluated in order to determine by how much the parameters 35 must be adjusted and in what direction. Such a procedure for error feedback is well-known in the prior art particularly in the field of neural networks and will not therefore be described in greater detail.

If determination is to take place directly on the basis of X-ray attenuation information, in particular the explained training can be modified for this purpose such that the training data sets contain X-ray attenuation information instead of the respective (mass) density information.

In general, the method according to an embodiment of the invention can also be described as explained below. Without limiting generality, a method for determining the patient weight using three steps described in the following will first be proposed here:

1. Determining a surface model O of the entire patient, e.g. using an optical 3D camera.
   [A 3D camera is present in more recent CT systems for the purpose of patient positioning and planning of the scan or topogram. The patient model (avatar) which in particular comprises a surface model, is created, for example, by machine learning based methods.]
2. Determining (mass) density information $\{L\rho\}$ of at least part of the patient using an X-ray projection measurement.
   [This can also be represented by a topogram in a CT system. A topogram, at least of the segment of the body to be examined, is available in the normal sequence of a CT examination in order to precisely define the actual scanning area, i.e. no additional radiation needs to be applied for weight determining purposes using the method according to an embodiment of the invention.]
3. Calculating a total patient weight using the surface model O from (1.) and the partial density information $\{L\rho\}$ from (2.).

The mass density information is not directly available from an X-ray measurement, but only the signal attenuation along the measured rays for the X-ray energy used. The mass density must therefore be derived. In the simplest case this is done by mapping the attenuation line integrals to mass density line integrals, comparable with the mapping to calculate electron densities for radiation therapy planning. A specific embodiment of the method step (2.) looks at like this:

Measurement of signal attenuations for a known X-ray spectrum, which corresponds to a regular projection image or a topogram. As the result, (generally polychromatic) line integrals $$L_\mu = -\ln(I/I_0) = -\ln(\int I(E)\exp(-\int\mu(E,\vec{r})d\vec{r})dE/\int I(E)dE)$$

for the measured rays are present.

Beam hardening correction of the line integrals (=linearization or monochromatization) by mean of mapping $$L_\mu' = f(L_\mu),$$

in order to enable the line integrals to be expressed (approximately) in the form $$L_\mu' \approx \int \mu'(\vec{r})d\vec{r} \quad (*).$$

This is a known step in CT reconstruction, based on the assumption that all the materials present in the body are in leading order watery.

The mapping f (x) is e.g. a polynomial $$f(x) = \sum_k a_k x^k$$

with coefficients matched to the spectrum, so that (*) is fulfilled.

(Approximate) interpretation of the different attenuations as pure density differences, i.e.

$$L'_\mu \approx \int \mu'(\vec{r})d\vec{r} \approx \mu_{H_2O} \int \rho(\vec{r})/\rho_{H_2O}(\vec{r})d\vec{r} = \mu_{H_2O}/\rho_{H_2O}(\vec{r}) \underbrace{\int \rho(\vec{r})d\vec{r}}_{=L_\rho}.$$

As a result, mass density line integrals $$L_\rho \approx L_\mu' \cdot \rho_{H_2O}/\mu_{H_2O} = \rho_{H_2O}/\mu_{H_2O} \cdot f(L_\mu)$$

can be specified, or more correctly a set {Lρ} of all the measured rays.

Regarding 3: The patient weight is preferably calculated with the aid of a machine learning based approach (e.g. a convolutional neural network) using the surface model O and the density information {Lρ} as input data and the patient weight as output. For this purpose the network must be trained using a plurality of data sets consisting of the input O, {Lρ} and using a known patient weight (e.g. using a calibrated weighing scales).

The proposed method uses information (3D camera and topogram) determined in the regular CT workflow in order to determine additional relevant patient information without influencing/interfering with the examination sequence. No additional hardware that would increase the equipment costs is required.

Compared to existing or proximate concepts wherein the surface model determined using a 3D camera is used to estimate the patient weight, the proposed approach uses another information source which enables the density distribution to be inferred directly. This is advantageous as, even in the case of identical body surface area, the weight may vary due to e.g. a different percentage of fat.

Instead of the patient weight, the body mass index (BMI) can also (or additionally) be determined. For this purpose the BMI can be used as another output in the training for the machine learning algorithm in step (3.).

Instead of projection images, the reconstructed image data of a native CT scan can also be used in step (2.). Not only density line integrals, but even a spatial density distribution is then available. In this case the initially reconstructed attenuation distribution (CT values) must be transformed into mass density values. The simplest implementation is to map CT values to mass density values, known from the radiation therapy planning. Alternatively, mass density distributions can be reconstructed directly using multimaterial decompositions. These are known from DE 102016209674A1, for example, the entire contents of which are hereby incorporated herein by reference.

In the case of multienergy topograms or CT images, in particular using photon-counting detectors, there are also known methods for calculating mass density line integrals or spatial mass density distributions on the basis of material decompositions [R. E. Alvarez and A. Macovski, "Energy-selective reconstructions in X-ray computerized tomography," Phys. Med. Biol., 21 (5), pp. 733-744, 1976], [Williamson et. al., "On two-parameter models of photon cross sections: Application to dual-energy CT imaging," Med. Phys. 33 (11), pp. 4115-4129, 2006], the entire contents of each of which are hereby incorporated herein by reference.

Although the invention has been illustrated and described in detail by the preferred example embodiment, the invention is not limited by the examples disclosed and other variations will be apparent to persons skilled in the art without departing from the scope of protection sought for the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining at least one of a total patient weight or a body mass index of a patient, the method comprising:
   acquiring image data including depth information of the patient;
   generating a surface model of the patient based on the image data;
   determining density information or X-ray attenuation information of at least part of the patient; and
   determining at least one of the total patient weight or the body mass index of the patient using a machine learning based approach with (i) the surface model and (ii) the density information or X-ray attenuation information, as input data.

2. The method of claim 1, wherein the acquiring acquires the image data using an optical 3D camera.

3. The method of claim 2, wherein the determining density information comprises:
   determining the density information from an X-ray measurement of the patient.

4. The method of claim 3, wherein the determining the density information comprises:
   determining the density information from X-ray projection data or from reconstructed image data.

5. The method of claim 4, wherein the X-ray projection data is X-ray projection data of a topogram image or the reconstructed image data is reconstructed image data of a native CT scan.

6. The method of claim 4, further comprising:
   correcting the X-ray projection data by beam hardening correction, and wherein
   the density information is determined from the X-ray projection data corrected by beam hardening correction.

7. The method of claim 1, wherein the determining density information comprises:
   determining the density information from an X-ray measurement of the patient.

8. The method of claim 7, wherein the determining the density information comprises:
   determining the density information from X-ray projection data, or from reconstructed image data.

9. The method of claim 8, further comprising:
   correcting the X-ray projection data by beam hardening correction, and wherein
   the density information is determined from the X-ray projection data corrected by beam hardening correction.

10. The method of claim 9, wherein the determining the density information from X-ray projection data comprises:
    calculating, for each pixel of the X-ray projection data, an integrated density as the density information from the X-ray projection data or the corrected X-ray projection data on an assumption of a same irradiated material.

11. The method of claim 8, wherein the determining the density information from X-ray projection data comprises:
    calculating, for each pixel of the X-ray projection data, an integrated density as the density information from the X-ray projection data on an assumption of a same irradiated material.

12. The method of claim 11, wherein the material is water.

13. The method of claim 8, wherein the X-ray projection data is X-ray projection data of a topogram image or the reconstructed image data is reconstructed image data of a native CT scan.

14. The method of claim 1, wherein at least one of (i) the determining density information or X-ray attenuation information and (ii) the determining at least one of the total patient weight or the body mass index of the patient, is performed using a machine learning method.

15. The method of claim 14, wherein the machine learning method uses a trained algorithm.

16. A non-transitory computer program product including a non-transitory computer-readable medium storing a computer program, the computer program including program sections that, when executed by at least one of a control device or a computing apparatus, cause the at least one of the control device or the computing apparatus to perform the method of claim 1.

17. A non-transitory computer-readable medium, storing a computer program including program sections, the program sections readable and executable by at least one processor, to carry out the method of claim 1 upon the program sections of the computer program being executed by the at least one processor.

18. The method of claim 1, wherein the determining density information or X-ray attenuation information comprises:
    determining partial density information or X-ray attenuation information of at least part of the patient.

19. The method of claim 18, wherein the determining of the at least one of the total patient weight or the body mass index of the patient comprises:
    determining the at least one of the total patient weight or the body mass index using the surface model and the partial density information or X-ray attenuation information.

20. An apparatus for determining at least one of a total patient weight or a body mass index of a patient, the apparatus comprising:
    a first interface to acquire image data including depth information of the patient;
    a generating unit to generate a surface model of the patient based on the image data;
    a second interface to acquire density information or X-ray attenuation information of at least part of the patient;
    a calculating unit to determine at least one of the total patient weight or the body mass index of the patient using a machine learning based approach with (i) the surface model and (ii) the density information or X-ray attenuation information of at least part of the patient, as input data; and
    an output unit to output the at least one of the total patient weight or the body mass index of the patient.

21. The apparatus of claim 20, wherein the first interface to includes an optical 3D camera.

22. An apparatus for determining at least one of a total patient weight or a body mass index of a patient, the apparatus comprising:

at least one interface to
acquire image data including depth information of the patient, and
acquire density information or X-ray attenuation information of at least part of the patient;
at least one processor to
generate a surface model of the patient based on the image data; and
determine at least one of the total patient weight or the body mass index of the patient using a machine learning based approach with (i) the surface model and (ii) the density information or X-ray attenuation information of at least part of the patient, as input data; and
an output device to output the at least one of the total patient weight or the body mass index of the patient.

23. The apparatus of claim 22, wherein the at least one interface includes an optical 3D camera to acquire the image data.

* * * * *